(12) United States Patent
DeRiso, II et al.

(10) Patent No.: US 10,098,780 B2
(45) Date of Patent: Oct. 16, 2018

(54) SLEEP APNEA PREVENTION

(71) Applicants: Anthony J. DeRiso, II, Sandusky, OH (US); Albert N. Santilli, Pepper Pike, OH (US)

(72) Inventors: Anthony J. DeRiso, II, Sandusky, OH (US); Albert N. Santilli, Pepper Pike, OH (US)

( * ) Notice: Subject to any disclaimer, the term of this patent is extended or adjusted under 35 U.S.C. 154(b) by 873 days.

(21) Appl. No.: 14/471,849

(22) Filed: Aug. 28, 2014

(65) Prior Publication Data
US 2016/0058607 A1    Mar. 3, 2016

(51) Int. Cl.
*A61F 5/56* (2006.01)

(52) U.S. Cl.
CPC ...................... *A61F 5/56* (2013.01)

(58) Field of Classification Search
CPC ........................................................ A61F 5/56
See application file for complete search history.

(56) References Cited

U.S. PATENT DOCUMENTS

| | | | |
|---|---|---|---|
| 1,587,558 A * | 6/1926 | Sheffield | ............... A45D 44/22 128/848 |
| 4,901,737 A | 2/1990 | Toone | |
| 5,092,346 A | 3/1992 | Hays et al. | |
| 5,361,416 A * | 11/1994 | Petrie | ....................... A42B 3/08 2/171 |
| 5,365,945 A | 11/1994 | Halstrom | |
| 5,427,117 A | 6/1995 | Thornton | |
| 5,462,066 A | 10/1995 | Snyder | |
| 5,566,683 A | 10/1996 | Thornton | |
| 5,570,704 A | 11/1996 | Buzzard et al. | |
| 5,687,743 A * | 11/1997 | Goodwin | .................. A61F 5/56 128/848 |
| 5,794,627 A | 8/1998 | Frantz et al. | |
| 5,810,013 A | 9/1998 | Belfer | |
| 5,921,241 A | 7/1999 | Belfer | |
| 6,129,084 A | 10/2000 | Bergersen | |
| 6,918,394 B2 * | 7/2005 | Matsuda | ................... A61F 5/56 128/848 |
| 7,174,895 B2 | 2/2007 | Thornton et al. | |
| 7,225,811 B2 | 5/2007 | Ruiz et al. | |
| 8,770,196 B2 * | 7/2014 | Peake | ................... A61M 16/00 128/207.11 |

(Continued)

*Primary Examiner* — Tarla Patel
(74) *Attorney, Agent, or Firm* — Wayne D. Porter, Jr.

(57) ABSTRACT

A method and apparatus for sleep apnea prevention includes a clamp that has an upper clamp segment having a distal end and a hinge end, the distal end being is adapted to engage the patient's upper lip adjacent the nose and a lower clamp segment having a distal end and a hinge end, the distal end being adapted to engage the patient's lower jaw behind the mandibular symphysis. A hinge connects the upper and lower segments at the hinge ends. The upper and lower segments apply force to the patient's face and jaw such that the lower jaw is moved upwardly and forwardly. Adjustable force can be applied by elastic members connected to the upper and loser segments. Alternatively, the hinge can be held in a desired position by a hand-adjustable nut and bolt. The distal end of the upper clamp segment can include portions that project laterally and upwardly in order to apply compressive force to a patient's face on either side of the patient's nose.

16 Claims, 5 Drawing Sheets

(56) References Cited

U.S. PATENT DOCUMENTS

2006/0005840 A1* 1/2006 Cannon ............ A61M 16/0683
  128/207.11
2007/0209663 A1* 9/2007 Marque ............ A61M 16/0683
  128/207.11

* cited by examiner

SLEEP APNEA PREVENTION

1. REFERENCE TO PRIOR APPLICATION

The present application is a continuation-in-part of, and claims priority from, application Ser. No. 13/594,625, filed Aug. 24, 2012 by Anthony J. DeRiso II and Albert N. Santilli, entitled Sleep Apnea Prevention, now U.S. Pat. No. 9,775,739 B2, issued Oct. 3, 2017, which claimed priority from provisional application Ser. No. 61/528,115, filed Aug. 26, 2011 by Anthony J. DeRiso II and Albert N. Santilli, entitled Sleep Apnea Prevention, the disclosures of which are incorporated herein by reference for all purposes.

BACKGROUND OF THE INVENTION

2. Field of the Invention

The present invention relates to the field of preventing snoring and sleep apnea, specifically, obstructive sleep apnea (OSA).

3. Description of the Prior Art

Snoring and sleep apnea are common sleep disorders caused by muscle relaxation and a narrowed pharynx. During sleep, the lower jaw muscles relax and in response the soft palate, uvula, and tongue relax and move to the back of the oral cavity. Consequently, the pharynx narrows. The air passing through a narrowed pharynx may cause the throat to vibrate which causes snoring.

In some people, the pharynx closes so much that enough air can't get through to the lungs. When this happens, the brain sends an alarm to open the airway. Most often, this is associated with a brief arousal from sleep. The brain quickly re-activates the muscles that hold the throat open, air passes through again, and the brain goes back to sleep. The repetitive episodes of complete or partial blockage of breathing are characteristic of obstructive sleep apnea (OSA). According to the American Sleep Apnea Association, more than 12 million Americans suffer from sleep apnea and it is estimated that 10 million remain undiagnosed. If sleep apnea is untreated, it can cause high blood pressure, weight gain, cardiovascular disease, and memory problems to name a few.

There are a variety of treatments to prevent sleep apnea and snoring. Drugs such as muscle relaxants have been used in an attempt to prevent closure of the pharynx during sleep. Masks of various sorts have been used in an attempt to provide gas under positive pressure to the pharynx so that breathing can be maintained. Numerous mechanical approaches also have been attempted. Typically, these involve some sort of dental appliance that is inserted into the mouth and that moves the lower jaw forward relative to the maxilla. By repositioning the lower jaw in a forward position, it is believed that the breathing passage will be kept open during sleep, thereby preventing both snoring and sleep apnea.

Mandibular advancement devices, dental appliances or oral mandibular advancement devices prevent the tongue from blocking the throat and/or advance the lower jaw forward and help keep the airway open during sleep. Other types of treatments range from behavior and lifestyle changes, mechanical therapy, mandibular advancement devices or surgery.

There are several problems with the foregoing approaches. Generally, the use of drugs is undesirable for a number of reasons, including possible dependence on such drugs. Masks with hoses are not well-tolerated and providing a source of pressurized gas can be complex and expensive. With respect to mechanical devices, often it is necessary for a custom-fit appliance to be used, which increases the cost to the patient. Prolonged use of such an appliance also has been reported to permanently change the bite characteristics of the patient.

SUMMARY OF THE INVENTION

The present invention provides a method and apparatus that addresses the foregoing concerns. The apparatus includes an external clamp that has a first pad that engages the upper lip beneath the nose and a second pad that engages the lower jaw on its underside, behind the chin (behind the mandibular symphysis). The pads are connected to each other by a flexible member, or brace. Preferably the second pad is rounded on that portion that contacts the lower jaw. The clamp is held in place by one or more straps, braces or springs. The clamp is held such that it presses against the upper lip while closing the lower jaw and pulling it forwardly and upwardly using relatively small forces.

In alternative embodiments, the brace can be provided with a spring to assist moving the first and second pads toward each other. If desired, the brace can be provided in two segments that are connected by a hinge. The two segments can be connected by a spring in order to assist in moving the first and second pads toward each other.

In another embodiment, a hand-adjustable bolted fastener can be provided to tighten the two segments in a desired fixed position, thereby eliminating the need for a spring to provide a biasing force. Yet additionally, first and second projections (preferably padded) can be provided to extend laterally and upwardly from the first pad. The projections apply compressive force to the patient's face on either side of the patients' nose. This tripartite arrangement provides improved torque to hold the jaw in place to prevent/reduce apnea. The larger, rounded shape spreads the applied force over a larger area of the face to reduce pressure and to reduce discomfort.

One of the advantages of the invention is that nothing is disposed within the patient's mouth. Accordingly, nothing contacts the patient's teeth and there is little or no chance that the bite characteristics of the patient will change with prolonged use. Although the clamp and straps need to be adjusted to fit each individual patient, such adjustment should be easy to accomplish by the patient himself. Another advantage is that the patient's mouth is kept closed, thereby requiring breathing through the nose and lessening the chance that snoring will occur. Moreover, the invention is inexpensive to manufacture and avoids the use of an uncomfortable mask covering the patient's face.

DESCRIPTION OF THE PREFERRED EMBODIMENT

Figure 1:
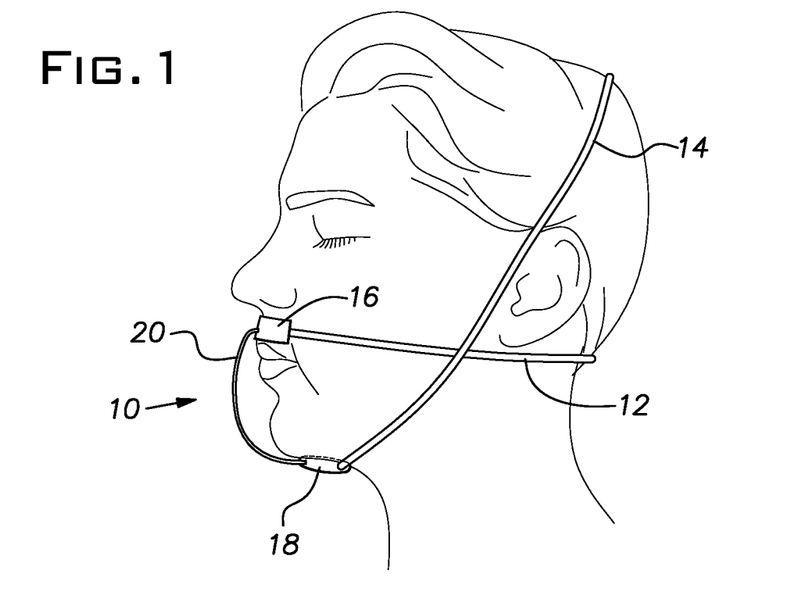
FIG. 1 is a side elevation view of a clamp according to the present invention engaging a patient's upper lip and lower jaw.

The current invention prevents snoring and sleep apnea by engaging a patient's upper lip and engaging the lower jaw on its underside, to gently pull the patient's jaw forwardly and upwardly. Referring to FIG. 1, a clamp 10 according to the current invention is shown. The clamp 10 is held in place on a patient's face by one or more braces, straps 12, 14 and/or springs. The clamp 10 comprises a first pad 16, engaging a patient's upper lip beneath the nose, and a second pad 18 engaging the lower jaw, on its underside. The second pad 18 may make contact to the underside of the lower jaw in the area of the anterior triangle, behind the mandibular symphysis. The configuration of the lower jaw in this region is in the nature of a small "hollow" that will receive the pad 18 and which will provide a surface against which force can be applied. Preferably, the second pad 18 is rounded on that portion that contacts the lower jaw.

The first pad 16 is connected to the second pad 18 via a brace 20 or flexible member that extends from the first pad 16, across the mouth, to the second pad 18. The brace 20 is curved to provide a space between the brace 20 and the patient, so the brace 20 does not lie uncomfortably on the patient's face. Preferably, the brace 20 is in the nature of a spring. The force of the brace 20 applied to the first and second pad 16, 18 causes gentle pressure against the upper lip while closing the lower jaw and gently pulling it forwardly and upwardly. This force also keeps the clamp 10 held in place on the patient's face. By pulling the lower jaw forwardly a small amount, the patient's breathing passage can be kept open during sleep. By pulling the lower jaw upwardly a small amount, the patient's mouth can be kept closed during sleep. The force applied by the brace 20 should be the minimum necessary to accomplish the foregoing objectives.

The clamp 10 may have one or more adjustable straps 12, 14 to provide additional support to the clamp 10. The additional support may help keep the clamp 10 in a comfortable position while the patient is sleeping. The straps 12, 14 may be connected to the first pad 16 and/or second pad 18 and extend around the patient's head.

Figure 2:
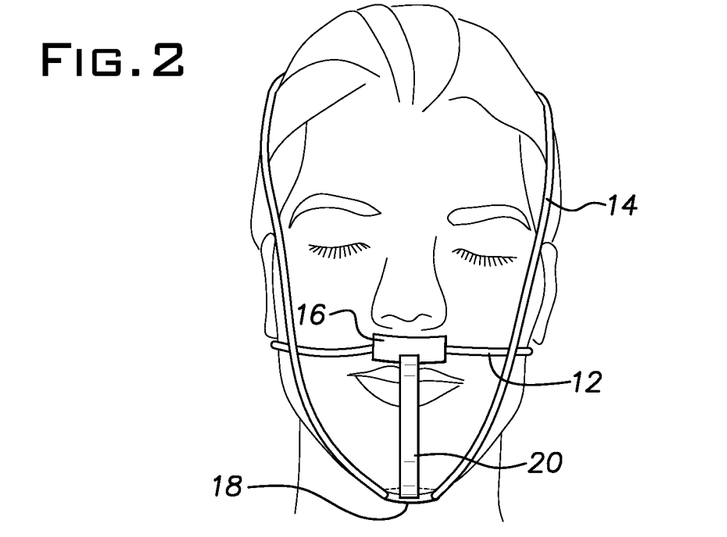
FIG. 2 is a front elevation view of the clamp of FIG. 1 engaging the patient's upper lip and lower jaw.
Figures 3, 4:
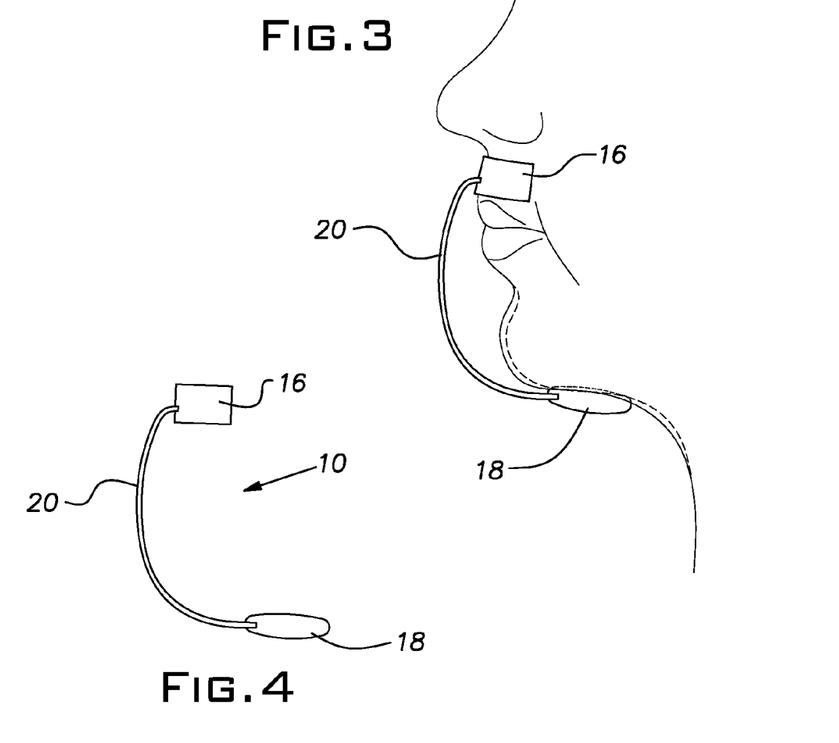
FIG. 3 is another side elevation view of the present invention engaging the patient's upper lip and lower jaw.
FIG. 4 is a side elevation view of a clamp according to the present invention with straps removed.

FIGS. 2-4 show additional views of the current invention. It is to be appreciated that the components of the clamp 10, including the first and second pad 16, 18, brace 20 and straps 12, 14, may be provided in various sizes or may be adjusted by the patient to provide a proper support and fit.

Figure 5:
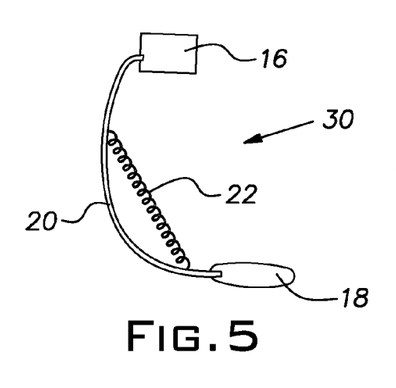
FIG. 5 is a view similar to FIG. 4 showing a spring used with a brace included as part of the clamp.

FIG. 5 is a view similar to FIG. 4 showing a second embodiment 30 that is similar to the embodiment 10 and which includes similar elements indicated by like reference numerals. In embodiment 30, a spring 22 is attached to the flexible brace 20 so as to urge the first and second pads 16, 18 toward each other. The positioning of the spring 22 and the strength of the spring 22 can be adjusted to suit the needs of the patient, more particularly to control the amount and direction of force being applied to the upper lip and lower jaw.

Figure 6:
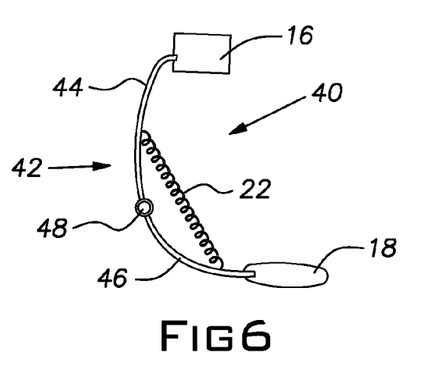
FIG. 6 is a view similar to FIG. 5 showing a hinged or articulated brace and a spring used therewith.

FIG. 6 is a view similar to FIG. 4 showing a third embodiment 40 that is similar to the embodiment 10 and which includes similar elements indicated by like reference numerals. In embodiment 40, a brace 42 includes a first segment 44 and a second segment 46 that are connected by a hinge 48. A spring 22 is attached to the segments 44, 46 so as to urge the first and second pads 16, 18 toward each other. The location of the hinge 48, the positioning of the spring 22 and the strength of the spring 22 can be adjusted to suit the needs of the patient, more particularly to control the amount and direction of force being applied to the upper lip and lower jaw.

Figures 7, 8:
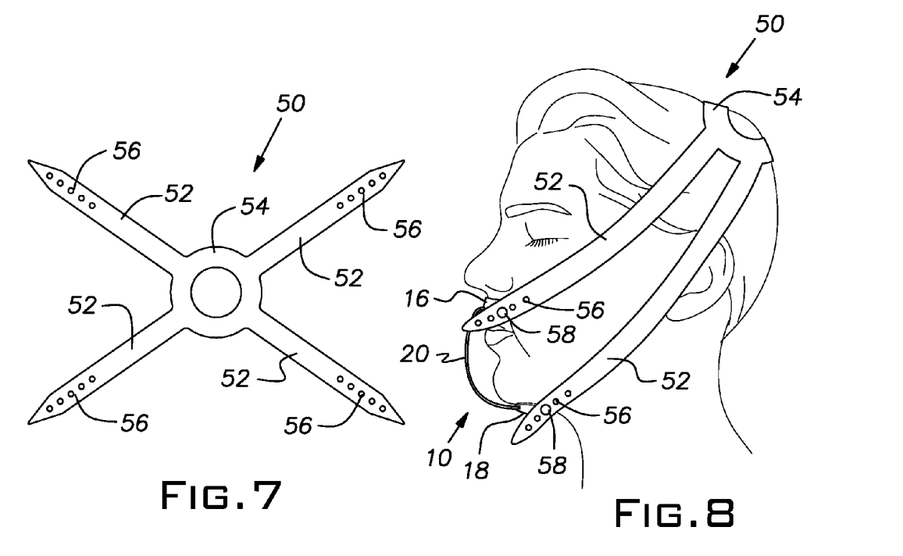
FIG. 7 is a view of a flexible strap that can be used as part of the clamp of the present invention.
FIG. 8 is a view showing the strap of FIG. 7 in use.

FIGS. 7 and 8 are views of a flexible strap 50 that can be used to hold the clamps 10, 30, 40 in place. The strap 50 preferably is made of rubber, although it can be made of any suitable flexible material that can conform to the shape of the patient's head. The strap 50 has four legs 52 that radiate outwardly from a ring 54. The legs include a plurality of openings 56 near their ends.

The ring 54 is adapted to fit about the crown of a patient's head. The legs 52 can be pulled about the sides of the patient's head. A plurality of pins 58 or other projections are included as part of the first and second pads 16, 18. The pins 58 can engage selected openings 56 in the legs 52. If the legs 52 and ring 54 are stretched slightly, they will hold the clamps 16, 18 firmly in place. It is believed that the strap 50 may be able to hold the clamps 16, 18 in place more securely than the straps 12, 14.

Figure 9:
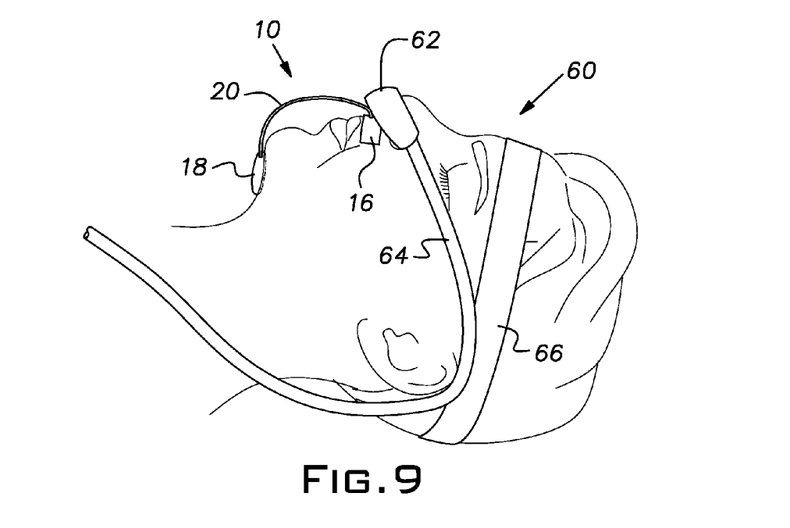
FIG. 9 is a view of the clamp of the present invention being used in conjunction with a breathing mask.

While the use of ventilators or masks preferably is avoided, nevertheless such accessories can be used with the present invention, if desired or necessary. FIG. 9 shows a fourth embodiment 60 in which the clamp 10 is used (the straps 12, 14 have been omitted for purposes of clarity of illustration). In this embodiment, a ventilator 62 is positioned beneath the patient's nose and is held in place by tubes 64 (only one of which is shown in FIG. 9). A headband 66 is fitted about the patient's head. The tubes 64 are connected to the headband 66. By this construction, air or other fluid can be supplied to the patient's nostrils while the clamp 10 is being used.

Figures 10, 11:
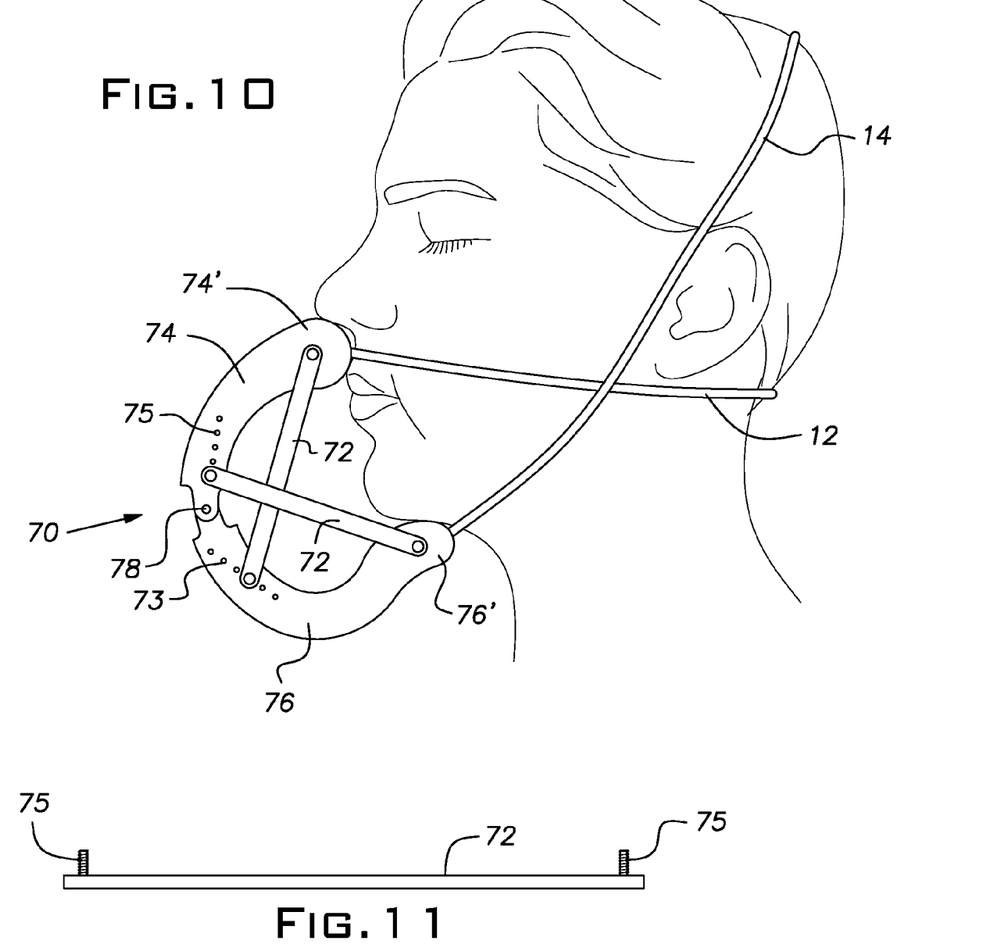
FIG. 10 is a side elevation view of a clamp according to an alternate embodiment of the present invention engaging a patient's upper lip and lower jaw.
FIG. 11 is a side elevation view of one of the bands shown in FIG. 10.

FIG. 10 is a view similar to FIG. 1 showing a fifth embodiment 70 that is similar to the embodiment 10 and which includes similar elements indicated by like reference numerals. In embodiment 70, a brace or clamp includes a first or upper segment 74 and a second or lower segment 76 that are connected by a hinge 78. The first segment 74 terminates in a first or distal end 74' that engages a patient's upper lip beneath the nose and functions similarly to the first pad 16 in FIG. 1. The second segment 76 terminates in a second or distal end 76' that engages the lower jaw, on its underside and functions similarly to the second pad 18 in FIG. 1.

Figure 12:
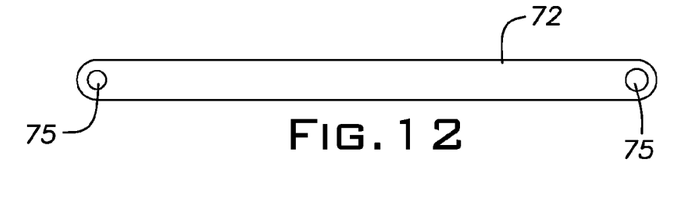
FIG. 12 is a top elevation view of one of the bands shown in FIG. 10.
Figure 13:
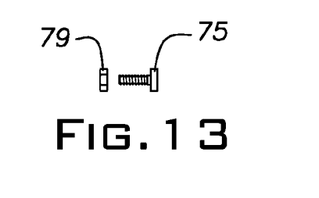
FIG. 13 is a view showing a screw used with a band in FIG. 11.

One or more elastic bands 72 are attached to the segments 74, 76 so as to urge the first and second ends 74', 76' toward each other. The bands 72 attach to the upper and lower clamp segments 74, 76 by means of pins or screws 75 (see also FIGS. 11-13) that fasten into adjustment holes 73 located along the length of each segment 74, 76, and are secured by a nut 79 (FIG. 13).

Preferably, the device uses two bands 72 on each side, for a total of four, but it is possible to have one band 72 per side, for a total of two. In addition, while elastic bands 72 are preferred, they could be replaced with rigid members 72 to hold the device 70 in a fixed position. The bands 72 apply force to the first and second segments 74, 76, which in turn apply force to the patient's face and jaw such that the lower jaw is moved upwardly and forwardly, which reduces or eliminates apnea. The location of the hinge 78, the positioning and number of the bands 72 and the strength of the bands 72 can be adjusted to suit the needs of the patient, more particularly to control the amount and direction of force being applied to the upper lip and lower jaw.

Figure 14:
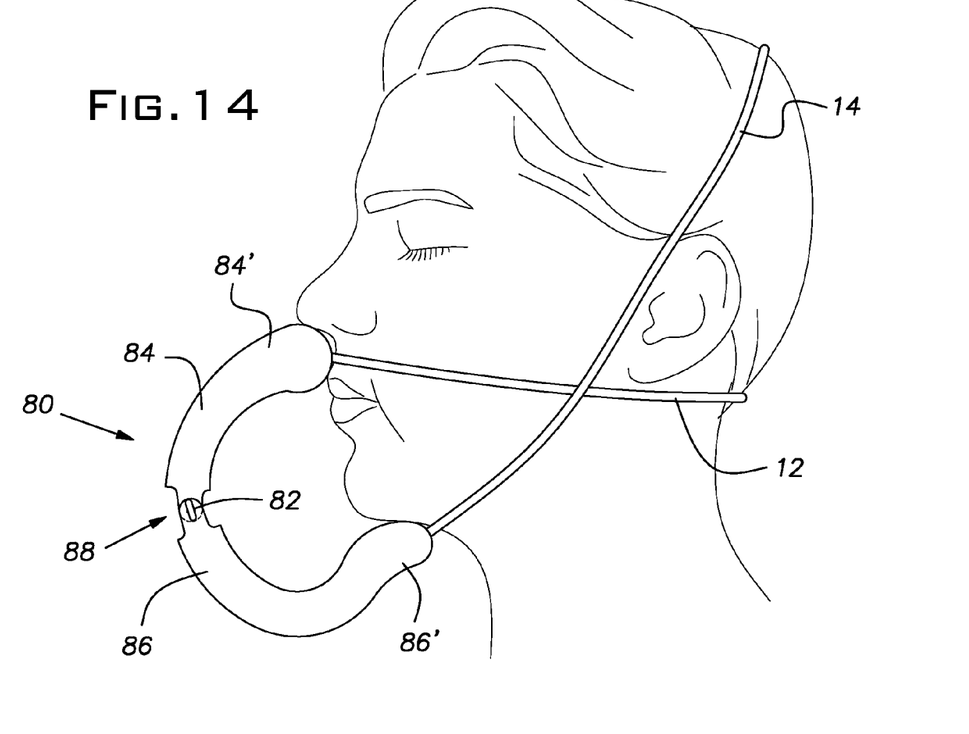
FIG. 14 is a side elevation view of a clamp according to an alternate embodiment of the present invention engaging a patient's upper lip and lower jaw.

FIG. 14 is a view similar to FIG. 10 showing a sixth embodiment 80 that is similar to the embodiment 70 and which includes similar elements indicated by like reference numerals. In embodiment 80, a brace or clamp includes a first/upper segment 84 and a second/lower segment 86 that are connected by a hinge 88. The upper segment 84 terminates in a first/distal end 84' that engages a patient's upper lip beneath the nose and functions similarly to the first pad 16 in FIG. 1. The lower segment 86 terminates in a second/distal end 86' that engages the lower jaw, on its underside and functions similarly to the second pad 18 in FIG. 1.

Figure 15:
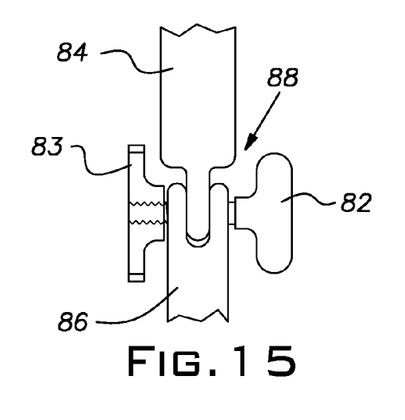
FIG. 15 is an enlarged front elevation view of a hinge and screw used with the embodiment of FIG. 14.

The hinge 88 is held together by a screw or bolt 82 and nut 83, which maintain the configuration of the device 80 and can be adjusted by the patient to provide a proper support and fit. The nut 83 and bolt 82 can be tightened to secure the clamp 80 in a fixed, specific configuration or position. Preferably, the screw 82 is a thumbscrew and the nut 83 is a wing-nut, such that both can be adjusted by hand, without the need for tools.

The device 80 is held in place via straps 12, 14 as discussed above. The location of the hinge 88, and the location and strength of the straps 12, 14 can be adjusted to suit the needs of the patient, more particularly to control the amount and direction of force being applied to the upper lip and lower jaw.

Figure 16:
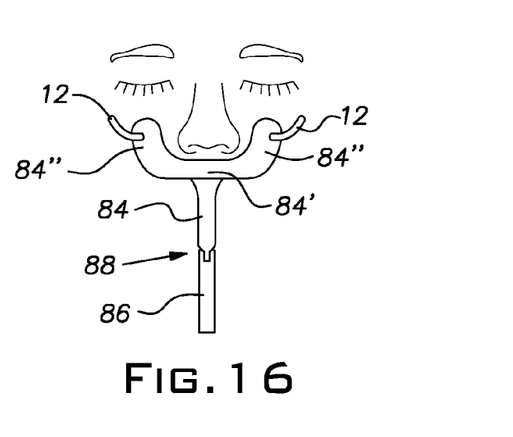
FIG. 16 is a front elevation view of the clamp of FIG. 14 engaging the patient's upper lip and lower jaw.

As shown in FIG. 16, the device 80 can include first and second projections 84'''' (preferably padded) that extend laterally and upwardly from upper segment 84. The projections 84'' apply compressive force to the patient's face on either side of the patients' nose. If desired, both embodiments 70 and 80 can have this tripartite arrangement of the first/upper segment 74, 84. This tripartite arrangement provides improved torque to hold the jaw in place to prevent/reduce apnea. The larger, rounded shape spreads the applied force over a larger area of the face to reduce pressure and to reduce discomfort.

It is expected that most or all of the components of the present invention can be made of inexpensive materials such as plastic, rubber, or similar materials. The use of such materials is expected to greatly decrease the cost of the device such that cost will not be a factor in a patient's acquisition of the device. Further, because the device is adjustable by the patient, it is expected that there will be no need to have custom-fit components. The avoidance of the use of custom-fit components is expected to reduce the cost of the device.

Although the present invention has been described in detail, it will be apparent to those skilled in the art that various changes and modifications can be made without departing from the true spirit and scope of the invention as hereinafter claimed. It is intended that all such changes and modifications be encompassed within the scope of the present disclosure and claims.

What is claimed is:

1. A clamp usable for sleep apnea prevention in a patient, comprising:
    an upper clamp segment having a distal end and a hinge end, wherein the distal end of the upper clamp segment is configured to engage the patient's upper lip adjacent the nose;
    a lower clamp segment having a distal end and a hinge end, wherein the distal end of the lower clamp segment is configured to contact the underside of the patient's lower jaw in the area of the anterior triangle behind the mandibular symphysis, wherein the distal end of the lower clamp segment is configured to be received in a small hollow of the patient's jaw and apply force against a surface of the patient's lower jaw;
    a hinge connecting said upper and lower clamp segments at the hinge ends, the hinge including a nut and bolt, the nut and bolt being capable of being tightened to secure the clamp in a specific, fixed configuration; and
    whereby said upper and lower clamp segments apply force to the patient's face and lower jaw such that the lower jaw is moved upwardly and forwardly.

2. The clamp of claim 1, further comprising:
    a first strap that passes about the back of the patient's head and having first and second ends, the first and second ends of the first strap being connected to the upper clamp segment so as to hold the upper clamp segment in place; and
    a second strap that passes about the upper rear portion of the patient's head and having first and second ends, the first and second ends of the second strap being connected to the lower clamp segment so as to hold the lower clamp segment in place.

3. The clamp of claim 1, wherein said nut and bolt are capable of being adjusted by hand without tools.

4. The clamp of claim 1, further including first and second portions that extend laterally and upwardly from the distal end of the upper clamp segment, the first portion configured to apply compressive force to the patient's face adjacent one side of the patient's nose and the second portion configured to apply compressive force to the patient's face adjacent the other side of the patient's nose.

5. The clamp of claim 1, wherein the upper and lower clamp segments are made of a plastics material.

6. The clamp of claim 1, wherein the length of the upper clamp segment and the lower clamp segment are such that the hinge is located in the region of the midpoint of the clamp.

7. The clamp of claim 1, wherein the upper clamp segment, the lower clamp segment, and the hinge are configured to be centrally positioned relative to the patient's face and configured to extend across the patient's mouth.

8. A method for preventing sleep apnea in a patient, comprising the steps of:
    providing a clamp having first and second ends;
    providing a hinge in the region of the midpoint of the clamp so as to divide the clamp into upper and lower segments, the hinge including a nut and bolt;
    placing the first end of the clamp against the patient's upper lip adjacent the nose;
    placing the second end of the clamp against the underside of the patient's lower jaw in the area of the anterior triangle behind the mandibular symphysis, wherein the second end of the clamp is received in a small hollow of the patient's jaw and is capable of applying force against a surface of the patient's lower jaw;

applying force to the patient's lower jaw through the second end such that the patient's lower jaw is moved upwardly and forwardly; and tightening the nut and bolt to secure the clamp in a specific, fixed configuration.

9. The method of claim 8, further comprising the steps of:
providing a first strap having first and second ends;
passing the first strap about the back of the patient's head;
connecting the first and second ends of the first strap to the first end of the clamp so as to hold the first end of the clamp in place;
providing a second strap having first and second ends;
passing the second strap about the back of the patient's head;
connecting the first and second ends of the second strap to the second end of the clamp so as to hold the second end of the clamp in place.

10. The method of claim 8, wherein the step of tightening the nut and bolt to secure the clamp in a specific, fixed configuration is accomplished by hand without tools.

11. The method of claim 8, further comprising the step of providing first and second portions that extend laterally and upwardly from a distal end of the upper clamp segment, the first portion configured to apply compressive force to the patient's face adjacent one side of the patient's nose and the second portion configured to apply compressive force to the patient's face adjacent the other side of the patient's nose.

12. The method of claim 8, wherein the clamp is centrally positioned relative to the patient's face and is configured to extend across the patient's mouth.

13. The method of claim 8, wherein the step of providing a clamp having first and second ends includes the step of making the clamp from a plastics material.

14. A clamp usable for sleep apnea prevention in a patient, comprising:

an upper clamp segment having a distal end and a hinge end, wherein the distal end of the upper clamp segment is configured to engage the patient's upper lip adjacent the nose;

a lower clamp segment having a distal end and a hinge end, wherein the distal end of the lower clamp segment is configured to contact the underside of the patient's lower jaw in the area of the anterior triangle behind the mandibular symphysis, wherein the distal end of the lower clamp segment is configured to be received in a small hollow of the patient's jaw and apply force against a surface of the patient's lower jaw;

a hinge connecting said upper and lower clamp segments at the hinge ends, the hinge including a nut and bolt, the nut and bolt being capable of being tightened by hand without tools to secure the clamp in a specific, fixed configuration;

the length of the upper clamp segment and the lower clamp segment being such that the hinge is located in the region of the midpoint of the clamp;

the upper clamp segment, the lower clamp segment, and the hinge being configured to be centrally positioned relative to the patient's face and configured to extend across the patient's mouth;

a first strap that passes about the back of the patient's head and having first and second ends, the first and second ends of the first strap being connected to the upper clamp segment so as to hold the upper clamp segment in place;

a second strap that passes about the upper rear portion of the patient's head and having first and second ends, the first and second ends of the second strap being connected to the lower clamp segment so as to hold the lower clamp segment in place; and whereby the upper and lower clamp segments apply force to the patient's face and jaw such that the lower jaw is moved upwardly and forwardly.

15. The clamp of claim 14, further including first and second portions that extend laterally and upwardly from the distal end of the upper clamp segment, the first portion configured to apply compressive force to the patient's face adjacent one side of the patient's nose and the second portion configured to apply compressive force to the patient's face adjacent the other side of the patient's nose.

16. The clamp of claim 14, wherein the upper and lower clamp segments are made of a plastics material.

* * * * *

UNITED STATES PATENT AND TRADEMARK OFFICE
CERTIFICATE OF CORRECTION

PATENT NO. : 10,098,780 B2
APPLICATION NO. : 14/471849
DATED : October 16, 2018
INVENTOR(S) : Anthony J. DeRiso, II et al.

Page 1 of 1

It is certified that error appears in the above-identified patent and that said Letters Patent is hereby corrected as shown below:

On the Title Page

Below Item (65) Prior Publication, insert:
--(63) Related U.S. Application Data
Continuation-in-part of Application No. 13/594,625, filed on August 24, 2012, which is now Patent No. 9,775,739, which is a non-provisional of Provisional Application No. 61/528,115, filed on August 26, 2011.--

Signed and Sealed this
Twenty-seventh Day of August, 2019

Andrei Iancu
*Director of the United States Patent and Trademark Office*